United States Patent [19]

Fleming

[11] 4,031,101

[45] June 21, 1977

[54] CIS-2, 6-DIMETHYL-α,α-DIPHENYL-1-PIPERIDINEBUTANOL COMPOUNDS

[75] Inventor: Robert Willerton Fleming, Ann Arbor, Mich.

[73] Assignee: Parke, Davis & Company, Detroit, Mich.

[22] Filed: Apr. 15, 1976

[21] Appl. No.: 677,094

[52] U.S. Cl. .......................... 260/293.84; 424/267
[51] Int. Cl.² ..................................... C07D 211/32
[58] Field of Search ............... 260/293.84; 424/267

[56] References Cited

UNITED STATES PATENTS

| | | | |
|---|---|---|---|
| 2,649,444 | 8/1953 | Barrett | 260/247.1 |
| 2,989,533 | 6/1961 | Stein et al. | 260/294.3 |
| 3,088,869 | 5/1963 | Zirkle | 167/55 |
| 3,375,278 | 3/1968 | Moffett | 260/570 |
| 3,423,511 | 1/1969 | Carlson et al. | 424/267 |
| 3,517,016 | 6/1970 | Pedrazzoli et al. | 260/294.3 |

OTHER PUBLICATIONS

CA.48:2112–2113 (1954), citation abstract of Brit. Pat. No. 683,950, (12–10–52).

*Primary Examiner*—Cecilia M. S. Jaisle
*Attorney, Agent, or Firm*—Stephen Raines; George M. Richards; David B. Ehrlinger

[57] ABSTRACT cis-2,6-Dimethyl-α,α-diphenyl-1-piperidinebutanol; and acid-addition salts. The compounds are pharmacological agents, especially antiarrythmic agents. The compounds can be produced by reacting phenyl lithium or phenylmagnesium halide with cis-γ-(2,6-dimethylpiperidino)butyrophenone or a lower alkyl ester of cis-2,6-dimethyl-1-piperidinebutyric acid; by reacting α-(3-halopropyl)-α-phenylbenzyl alcohol with cis-2,6-dimethylpiperidine, or by reacting cis-1-(3-lithiopropyl)-2,6-dimethylpiperidine with benzophenone.

3 Claims, No Drawings

CIS-2,6-DIMETHYL-α,α-DIPHENYL-1-PIPERIDINEBUTANOL COMPOUNDS

SUMMARY AND DETAILED DESCRIPTION

The present invention relates to new 1-piperidinebutanol compounds and methods for their preparation. More particularly, the invention relates to cis-2,6-dimethyl-α,α-diphenyl-1-piperidinebutanol which has the formula

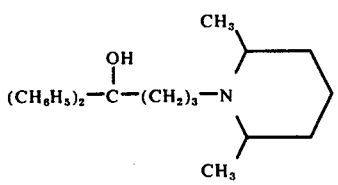

to salts thereof, and to methods for the production of the foregoing compounds.

In accordance with the invention, the foregoing compounds can be produced by reacting a compound of the formula

$C_6H_5-M$    II with a compound of the formula

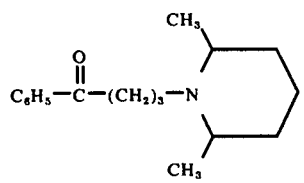

having a cis configuration, wherein M is Li, MgCl, MgBr or MgI, preferably lithium.

This reaction is generally carried out in a solvent such as an ether (diethyl ether, tetrahydrofuran, diethylene glycol dimethyl ether, etc.), a hydrocarbon (benzene, toluene, etc.), or mixtures thereof for periods of from one to 48 hours at from 0° to 60° C., preferably one to two hours at room temperature. The preferred solvent system employs a mixture of diethyl ether and tetrahydrofuran. When M is a magnesium halide, an ether is required.

While at least one mole of the phenylmetallic agent (II) should be used for each mole of piperidine compound (III), an excess of the phenylmetallic agent is preferred.

The intermediate metallic derivative of a compound of formula I is hydrolyzed under acidic (dilute aqueous hydrochloric acid, aqueous ammonium chloride, dilute aqueous sulfuric acid, etc.), neutral or basic (dilute aqueous sodium hydroxide, dilute aqueous potassium hydroxide, etc.) conditions, preferably under acidic or neutral conditions.

The product may be isolated as the free base or an acid-addition salt thereof by suitable adjustment of the pH.

The cis-γ-(2,6-dimethylpiperidino)butyrophenone is prepared by reacting an excess of cis-2,6-dimethylpiperidine with γ-chlorobutyrophenone, ethylene ketal in the presence of sodium iodide at reflux for about forty-eight hours, followed by treating an ether extract of the foregoing with concentrated hydrochloric acid and then a fifty percent aqueous sodium hydroxide solution.

The γ-chlorobutyrophenone, ethylene ketal is prepared by reacting γ-chlorobutyrophenone with ethylene glycol using p-toluenesulfonic acid as a catalyst. The reaction is carried out utilizing benzene as a solvent and a water trap coupled into the reaction system. The reaction mixture is refluxed until the desired amount of water is collected, followed by neutralization of the acid and removal of the solvent.

Also in accordance with the invention, the compounds of the invention can be prepared by reacting a compound of formula II with a compound of the formula

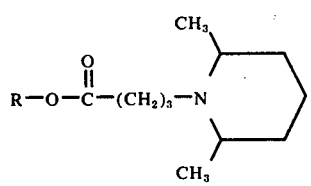

having a cis configuration wherein R is lower alkyl. Lower alkyl is intended to mean a hydrocarbon group having from one to six carbon atoms, such as methyl, ethyl, isopropyl, etc.

This reaction is generally carried out in a solvent such as an ether (diethyl ether, tetrahydrofuran, diethylene glycol dimethyl ether, etc.), a hydrocarbon (benzene, toluene, etc.), or mixtures thereof for periods of from one to 48 hours at from 0° to 60° C. The preferred solvent is ether, optionally including some benzene and when M is a magnesium halide an ether is required. When M is lithium, periods of from two to four hours at 5° to 30° C. are preferred, while when M is magnesium halide, twelve to forty-eight hours at 30° to 50° C. are preferred.

At least two moles of compound II are required per mole of ester of compound IV and an even larger excess of compound II is preferred.

The intermediate metallic derivative of a compound of formula I is hydrolyzed under acidic (dilute aqueous hydrochloric acid, aqueous ammonium chloride, dilute aqueous sulfuric acid, etc.), neutral or basic (dilute aqueous sodium hydroxide, dilute aqueous potassium hydroxide, etc.) conditions, preferably under acidic or neutral conditions.

The product may be isolated as the free base or an acid-addition salt thereof by suitable adjustment of the pH.

The cis-2,6-dimethyl-1-piperidinebutyric acid, lower alkyl esters are prepared by reacting lower alkyl 4-chlorobutyrates with an excess of cis-2,6-dimethylpiperidine in the presence of sodium iodide. The reaction is carried out in refluxing xylene for a period of time of about forty-four hours.

In addition, in accordance with the invention, the compounds of the invention can be prepared by reacting a compound of the formula

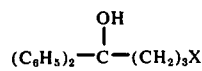

with cis-2,6-dimethylpiperidine (VI) wherein X is chlorine, bromine or iodine in the presence of a base, such as alkali metal hydroxides, alkali metal carbonates, alkali metal alkoxides, strongly basic tertiary amines or an excess of the amine reactant, cis-2,6-dimethylpiperidine (VI). The preferred base is the amine of the formula VI.

While the preferred solvent is xylene, numerous suitable solvents may be employed, such as hydrocarbons (benzene, toluene, etc.), ethers (dibutyl ether, dioxane, tetrahydrofuran, diethylene glycol dimethyl ether, etc.), tertiary amides (dimethylformamide, N,N-dimethylacetamide, etc.); and mixtures thereof.

The reaction is conducted for from twelve to seventy-two hours at about 50° to about 200° C., preferably twenty-four to fifty hours at 130° to 150° C. using an excess of the amine of the formula VI when compared to the quantity of halocarbinol of the formula V employed.

The product may be isolated as the free base or an acid-addition salt thereof by suitable adjustment of the pH.

Lastly, in accordance with the invention, the compounds of the invention can be prepared by reacting a compound of the formula

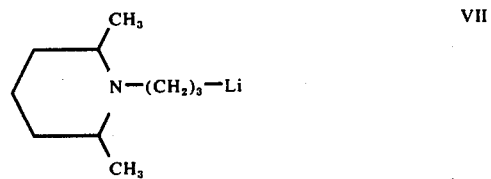

with benzophenone in a suitable solvent such as an ether (diethyl ether, tetrahydrofuran, diethylene glycol dimethyl ether, etc.) for from four hours to twenty-four hours at 0° to 60° C. The preferred reaction conditions employ tetrahydrofuran as the solvent and a reaction time of from twelve hours to eighteen hours at a temperature range of from 20° to 35° C.

It is preferred to use approximately equivalent amounts of the lithium derivative of structure VII and benzophenone.

The intermediate metallic derivative of a compound of formula I is hydrolyzed under acidic (dilute aqueous hydrochloric acid, aqueous ammonium chloride, dilute aqueous sulfuric acid, etc.), neutral or basic (dilute aqueous sodium hydroxide, dilute aqueous potassium hydroxide, etc.) conditions, preferably under acidic or neutral conditions.

The product may be isolated as the free base or an acid-addition salt thereof by suitable adjustment of the pH.

The cis-1-(3-lithiopropyl)-2,6-dimethylpiperidine is prepared by reacting one equivalent of cis-1-(3-chloropropyl)-2,6-dimethylpiperidine with two equivalents of lithium over a six-hour period in tetrahydrofuran. After filtration, the remaining solution is reacted directly with benzophenone.

The cis-1-(3-chloropropyl)-2,6-dimethylpiperidine is prepared by reacting thionyl chloride with cis-2,6-dimethyl-1-piperidinepropanol in benzene at a temperature of from 0° to 5° C. for thirty minutes followed by two hours at reflux. The chlorinated product is isolated as the hydrochloride by filtration.

The cis-2,6-dimethyl-1-piperidinepropanol is prepared by reacting 3-bromopropanol with an excess of cis-2,6-dimethylpiperidine in refluxing xylene for a period of about two hours. The cis-2,6-dimethyl-1-piperidinepropanol is separated by distillation.

The free base of formula I forms acid-addition salts, which are also part of this invention, with any of variety of inorganic and organic acids. Pharmaceutically-acceptable acid-addition salts are formed with such acids as hydrochloric, hydrobromic, sulfuric, sulfamic, nitric, phosphoric, acetic, citric, tartaric, succinic, oxalic, benzoic, maleic, malic, lactic, gluconic, naphthalene-1,5-disulfonic, methanesulfonic, p-toluenesulfonic, and pamoic acids. The free bases and their salt forms are interconvertible by adjustment of the pH. They differ in solubility properties but are otherwise equivalent for the purposes of the invention.

The compounds of the invention can exist in anhydrous form as well as in solvated, including hydrated, forms. In general, the hydrated forms and the solvated forms with pharmaceutically-acceptable solvents are equivalent to the anhydrous or unsolvated form for the purposes of the invention.

The compounds of the invention are new chemical compounds of value as pharmacological agents. More specifically, these compounds are antiarrhythmic agents. The activity of these compounds is shown by way of the following antiarrhythmic screen.

Dogs were operated on according to the procedure reported in Circulation 1, 1318 (1950). cis-2,6-Dimethyl-α,α-diphenyl-1-piperidinebutanol, lidocaine and quinidine were tested intravenously nineteen to twenty-four hours after coronary artery ligation. The degree of effectiveness of the compound was determined by the degree of conversion of ventricular ectopic beats to sinus beats. The table shown below gives the results of the screen performed on cis-2,6-dimethyl-α,α-diphenyl-1-piperidinebutanol and the known antiarrhythmic agents, lidocaine and quinidine.

TABLE

| Compound | Dose* | Time Post Dose | % Conversion |
| --- | --- | --- | --- |
| Lidocaine | 10 mg/kg i.v. | 5 min. | 92 |
| | | 20 min. | 0 |
| | | 55 min. | 0 |
| Quinidine | 20 mg/kg i.v. | 5 min. | 66 |
| | | 20 min. | 35 |
| | | 55 min. | 41 |
| cis-2,6-Dimethyl-α,α-diphenyl-1-piperidine-butanol | 5 mg/kg i.v. | 2 min. | 97 |
| | | 20 min. | 87 |
| | | 55 min. | 88 |

*Dose calculated as free base tested as salts.

The invention is illustrated by the following examples:

EXAMPLE 1

A solution of 51 g. of cis-γ-(2,6-dimethylpiperidino)-butyrophenone in 200 ml. of tetrahydrofuran is added with stirring over a one hour period to a solution of phenylmagnesium bromide, prepared from 6.1 g. of magnesium and 39.3 g. of bromobenzene, in 125 ml. of dry ether. After the addition is complete, the mixture is stirred and heated at reflux for 20 hours, then cooled and treated slowly with 30 ml. of saturated aqueous ammonium chloride. The mixture is filtered and the filtrate evaporated at reduced pressure. The residual syrup is dissolved in 500 ml. of 10 percent acetic acid and the solution is extracted with 100 ml. of ether, the extract being discarded. The acid solution is basified with aqueous sodium hydroxide and extracted with ether. The ether extract is washed with water, dried and treated with a slight excess of a solution of dry hydrogen chloride in 2-propanol. The resulting precipitate of cis-2,6-dimethyl-α,α-diphenyl-1 -piperidinebutanol monohydrochloride is collected by filtration, washed with ether and dried; m.p. 235°–236° C. after crystallization from absolute ethanol.

Intermediates a. cis-γ-(2,6-Dimethylpiperidino)butyrophenone

A mixture of 619 g. of γ-Chlorobutyrophenone, ethylene ketal, 700 g. of cis-2,6-dimethylpiperidine and 16 g. of sodium iodide is stirred and heated at reflux for 48 hours. The mixture is cooled, diluted with 1 l. of anhydrous ether and filtered to remove cis-2,6-dimethylpiperidine hydrochloride. The filter cake is washed with 1 l. of ether and the filtrate and washings combined. The resulting ether solution is washed five times with 500 ml. portions of water, then extracted with a solution of 300 ml. of concentrated hydrochloric acid in 3 l. of water. The acid extract is washed with 500 ml. of ether, then heated to 70°–80° and allowed to cool to room temperature over a period of 16 hours. The resulting solution is basified with 50% aqueous sodium hydroxide and the organic layer is separated. The aqueous layer is extracted with 500 ml. of ether and the extract is combined with the organic layer. The combined extract is washed several times with water, dried and evaporated. The oily residue is distilled at reduced pressure to give cis-γ-(2,6-dimethylpiperidino)butyrophenone; b.p. 138°–141° C./0.1 mm.

b. γ-Chlorobutyrophenone, Ethylene Ketal

A mixture of 500 g. of γ-chlorobutyrophenone, 225 g. of ethylene glycol, 10 g. of p-toluenesulfonic acid and 1.5 l. of benzene is heated at reflux under a water separator until water collection ceases. The resulting solution is cooled, neutralized with 10 ml. of triethylamine and evaporated at reduced pressure to give γ-chlorobutyrophenone, ethylene ketal, suitable for use without further purification. (The pure material boils at 100°–118° C./0.1–0.8 mm. and melts at 57°–59° C.)

EXAMPLE 2

A 2M solution of phenyl lithium, 70 ml., in benzeneether (70–30) is added with stirring under a nitrogen atmosphere to 70 ml. of tetrahydrofuran. The mixture is stirred while a solution of 25.9 g. of cis-γ-(2,6-dimethylpiperidino)butyrophenone in 100 ml. of tetrahydrofuran is added dropwise over a period of 75 minutes. After the addition is complete, the mixture is stirred an additional 45 minutes, then treated slowly with 15 ml. of water. The supernatant liquid is decanted from the precipitated solid and evaporated at reduced pressure. The residual oil is dissolved in 100 ml. of petroleum ether and the solution is cooled to 0°–5° to crystallize cis-2,6-dimethyl-α,α-diphenyl-1-piperidinebutanol which is removed by filtration; m.p. 90°–91° C. after recrystallization from petroleum ether.

Methanesulfonic acid, 0.02 mole, in isopropanol, 8.0 ml., is added to crude cis-2,6-dimethyl-α,α-diphenyl-1-piperidinebutanol (m.p. 81°–87° C.), 5.5 g., in isopropanol, 25 ml. The mixture is warmed slightly to obtain a clear solution and diluted to 125 ml. with anhydrous ether. On cooling in an ice bath, 6.2 g. of cis-2,6-dimethyl-α,α-diphenyl-1-piperidinebutanol methanesulfonate salt is obtained; m.p. 168.5°–170° C. Further recrystallization from isopropanol, 40 ml., diluted with ether to 100 ml. gives 5.8 g. of product; 169°–170° C.

p-Toluenesulfonic acid monohydrate, 3.8 g., in methanol, 10 ml., is added to a solution of cis-2,6-dimethyl-α,α-diphenyl-1-piperidinebutanol, 6.8 g., in isopropanol, 25 ml. The mixture is warmed slightly to obtain a clear solution and diluted to 150 ml. with anhydrous ether. On cooling in an ice bath an oil separates which crystallizes on standing. The crystals are filtered off and recrystallized from isopropanol, 50 ml., and anhydrous ether, 50 ml., giving 7.6 g. of cis-2,6-dimethyl-α,α-diphenyl-1-piperidinebutanol p-toluenesulfonate; m.p. 156.5°–157.5° C. A second recrystallization gave 6.8 g. of product; m.p. 157°–157.5° C.

A solution of 6.8 g. of cis-2,6-dimethyl-α,α-diphenyl-1-piperidinebutanol in isopropanol, 25 ml., is treated with 2 ml. of 48 percent hydrobromic acid followed by dilution to 100 ml. with anhydrous ether. On cooling, 6.7 g. of cis-2,6-dimethyl-α,α-diphenyl-1-piperidinebutanol hydrobromide separates; m.p. 195°–196.5° C. The product is again recrystallized from ethanol 3A, 50 ml., diluted to 125 ml. with ether yielding 6.5 g.; m.p. 196°–197.5° C. A final recrystallization from a mixture of isopropanol, 75 ml., and methanol, 20 ml., gives 5.4 g.; m.p. 197.5°–198° C.

A solution of 6.8 g. of cis-2,6-dimethyl-α,α-diphenyl-1-piperidinebutanol in isopropanol, 25 ml., is treated with a solution of 2 g. of sulfamic acid in isopropanol, 25 ml. After heating and decanting off the liquid, the liquid is allowed to cool. cis-2,6-Dimethyl-α,α-diphenyl-1-piperidinebutanol sulfamate, 6.8 g., crystallized; m.p. 131°–132° C. A second recrystallization from isopropanol gives 6.8 g. of product; m.p. 131°–132° C.

EXAMPLE 3

A 2M solution of phenyl lithium in benzene-ether (70 to 30), 100 ml., is added to 100 ml. of dry ether with stirring under a nitrogen atmosphere. The mixture is stirred and cooled to 0°–5° while a solution of 20 g. of cis-2,6-dimethyl-1-piperidinebutyric acid, methyl ester, in 100 ml. of dry ether is added slowly over a period of 15 minutes. After the addition is complete, the mixture is stirred an additional 2.5 hours at 0°–5°, then treated dropwise with 30 ml. of water. The organic layer is separated, washed with water and extracted with an excess of dilute acetic acid. The acid extract is washed with ether, basified with aqueous sodium hydroxide, then extracted with ether. The ether extract is washed with water, dried and evaporated to give cis-2,6-dimethyl-α,α-diphenyl-1-piperidinebutanol; m.p. 90°–91° C. after two crystallizations from petroleum ether.

Intermediate cis-2,6-Dimethyl-1-piperidinebutyric Acid, Methyl Ester

A mixture of 273 g. of methyl 4-chlorobutyrate, 460 g. of cis-2,6-dimethylpiperidine, 10 g. of sodium iodide and 300 ml. of xylene is stirred and heated at reflux for 44 hours, then cooled and filtered. The filter cake is washed with xylene and the combined filtrate and washings are evaporated at reduced pressure to give cis-2,6-dimethyl-1-piperidinebutyric acid, methyl ester which is purified by distillation; b.p. 79°–81° C./0.5 mm.

EXAMPLE 4

A solution of 18.9 g. of cis-1-(3-chloropropyl)-2,6-dimethylpiperidine in 50 ml. of tetrahydrofuran is added dropwise under a nitrogen atmosphere to a stirred mixture of 1.4 g. of lithium wire and 50 ml. of tetrahydrofuran over a period of 2 hours. After the addition is complete, the mixture is stirred another 4 hours under nitrogen, the lithium metal removed manually and a solution of 18.2 g. of benzophenone in 70 ml. of tetrahydrofuran is added dropwise with stirring over a period of 2 hours. The mixture is stirred for 16 hours, then treated with 5 ml. of water. The organic phase is decanted from the precipitated solid and evaporated at reduced pressure. The residual gum is stirred with excess dilute acetic acid and ether. The acid layer is separated, washed with ether, basified with aqeuous sodium hydroxide and extracted with ether. The ether extract is washed with water, dried and treated with a slight excess of a solution of dry hydrogen chloride in 2-propanol. The resulting precipitate of cis-2,6-dimethyl-$\alpha,\alpha$-diphenyl-1-piperidinebutanol monohydrochloride is collected by filtration, washed with ether and dried; m.p. 234°–235° C. after crystallization from 2-propanol-ether.

Intermediates a. cis-1-(3-Chloropropyl)-2,6-dimethylpiperidine

A stirred solution of 171 g. of cis-2,6-dimethyl-1-piperidinepropanol in 400 ml. of benzene is cooled to 0°–5° and 143 g. of thionyl chloride is added dropwise over a period of 30 minutes. The mixture is then heated at reflux for 2 hours, cooled and diluted with 1 l. of ether. The resulting precipitate of cis-1-(3-chloropropyl)-2,6-dimethylpiperidine hydrochloride is collected by filtration; m.p. 173°–174° C. after crystallization from 2-propanol-ether. The free base is prepared as needed by dissolving the hydrochloride in a minimum amount of water, cooling and adding a slight excess of 50% aqueous sodium hydroxide. The liberated base is immediately extracted with several portions of benzene. The extracts are combined, dried and evaporated to give the free base, cis-1-(3-chloropropyl)-2,6-dimethylpiperidine.

b. cis-2,6-Dimethyl-1-piperidinepropanol

A stirred solution of 460 g. of cis-2,6-dimethylpiperidine in 300 ml. of xylene is treated with 278 g. of 3-bromopropanol over a period of 15 minutes. The mixture is stirred and heated at reflux for 2 hours, then allowed to cool while stirring for 16 hours. The mixture is filtered and the filtrate evaporated at reduced pressure. The residue is distilled at reduced pressure to give cis-2,6-dimethyl-1-piperidinepropanol; b.p. 147°–149° C./25 mm.

EXAMPLE 5

A mixture of 26 g. of $\alpha$-(3-chloropropyl)-$\alpha$-phenylbenzyl alcohol (British Pat. No. 683,950), 2 g. of sodium iodide, 28 g. of cis-2,6-dimethylpiperidine and 150 ml. of xylene is stirred and heated at reflux for 48 hours. The mixture is cooled, washed well with water and extracted with excess dilute acetic acid. The acid extract is washed with ether, basified with 50% aqueous sodium hydroxide and extracted with ether. The ether is washed with water, dried and treated with a slight excess of 10% methanesulfonic acid in 2-propanol. The resulting precipitate of cis-2,6-dimethyl-$\alpha,\alpha$-diphenyl-1-piperidinebutanol methanesulfonate is collected by filtration and washed with ether; m.p. 169°–170° C. after crystallization from 2-propanolether.

I claim:
1. cis-2,6-Dimethyl-$\alpha,\alpha$-diphenyl-1-piperidinebutanol and acid-addition salts thereof.
2. The compound of claim 1 having the name cis-2,6-dimethyl-$\alpha,\alpha$-diphenyl-1-piperidinebutanol hydrochloride.
3. The compound of claim 1 having the name cis-2,6-dimethyl-$\alpha,\alpha$-diphenyl-1-piperidinebutanol methanesulfonante.

* * * * *